(12) United States Patent
Richardson

(10) Patent No.: US 6,379,676 B2
(45) Date of Patent: Apr. 30, 2002

(54) ENHANCING IMMUNE RESPONSE IN ANIMALS

(75) Inventor: Kurt E. Richardson, Maysville, GA (US)

(73) Assignee: Anitox Corporation, Buford, GA (US)

( * ) Notice: Subject to any disclaimer, the term of this patent is extended or adjusted under 35 U.S.C. 154(b) by 0 days.

(21) Appl. No.: 09/265,821

(22) Filed: Mar. 10, 1999

(51) Int. Cl.⁷ .................................................. A61K 39/02
(52) U.S. Cl. ............................ 424/234.1; 424/184.1; 424/240.1; 424/241.1; 424/256.1; 424/258.1; 424/264.1; 424/232.1; 426/2; 426/335; 426/532; 426/302
(58) Field of Search .......................... 424/130.1, 150.1, 424/184.1, 234.1, 240.1, 241.1, 256.1, 258.1, 264.1, 232.1; 426/2, 335, 532, 302

(56) References Cited

U.S. PATENT DOCUMENTS

| 5,436,001 A | * | 7/1995 | Kramer | 424/93.4 |
| 5,505,976 A | | 4/1996 | Bland et al. | |
| 5,591,467 A | | 1/1997 | Bland et al. | |
| 5,641,492 A | * | 6/1997 | Sprouse et al. | 424/258.1 |
| 5,919,451 A | * | 7/1999 | Cook et al. | 424/130.1 |

OTHER PUBLICATIONS

Potter et al. J. Animal Science. 1985. 61(5): 1058–1065.*

* cited by examiner

*Primary Examiner*—Jennifer E. Graser
(74) *Attorney, Agent, or Firm*—Pillsbury Winthrop LLP

(57) ABSTRACT

A method for improving the immune response of an animal to a vaccine, comprising: feeding an animal a diet of contamination-resistant feed, and treating said animal with an anti-viral or anti-bacterial vaccine.

12 Claims, No Drawings

ENHANCING IMMUNE RESPONSE IN ANIMALS

BACKGROUND OF THE INVENTION

1. Field of the Invention

A method for enhancing the effectiveness of vaccines in animals, by maintaining the animals on a diet of contamination-resistant feed.

2. Discussion of the Background

Livestock such as poultry, swine, cattle and horses are routinely treated with vaccines to prevent viral and bacterial diseases. Breeders are sometimes vaccinated for another reason, to provide passive immunity to their offspring by supplying antibodies through colostrum in the case of mammals, and through egg yolk in the case of birds. Because neonatal animals have underdeveloped immune systems, passive immunity is their main source of protection against viral and bacterial diseases.

It is known that animal feed can be rendered highly resistant to contamination by pathogens, by spraying it with formaldehyde using an atomizing spray technique disclosed by Bland et al., U.S. Pat. No. 5,505,976 and divisional U.S. Pat. No. 5,591,467, both incorporated herein by reference. It was also disclosed that animals maintained on such feeds are more productive, in terms of feed conversion efficiency. It has now been discovered that animals which are maintained on a diet of contamination-resistant feedstuffs respond more strongly when immunized against diseases, with anti-viral vaccines and anti-bacterial vaccines (bacterins). Also, transference of passive immunity to offspring is enhanced by maintaining a breeder on contamination-resistant feedstuffs, providing a method for improving the health of neonatal animals.

SUMMARY OF THE INVENTION

An object of the invention is to provide a method for improving the immune response of an animal to a vaccine by maintaining it on a diet of contamination-resistant feed and treating the animal with an anti-viral or anti-bacterial vaccine.

Another object of the invention is to provide a method for increasing the level of antibodies in eggs, colostrum or milk produced in response to vaccination, by maintaining a breeding animal on a diet of contamination-resistant feed, and treating the breeding animal with an anti-viral or anti-bacterial vaccine.

Another object is to improve the absorption of antibodies by neonatal animals from egg yolk, colostrum or milk, by maintaining a breeding animal on a diet of contamination-resistant feed, vaccinating the breeder with an effective amount of an anti-viral or anti-bacterial vaccine and administering the resulting egg yolk, colostrum or milk to a neonatal animal.

DETAILED DESCRIPTION OF THE PREFERRED EMBODIMENTS

When an animal is maintained on a diet of contamination-resistant feedstuffs, produced by treatment with formaldehyde in accordance with the methods of Bland et al., subsequent vaccinations of the animal with standard anti-viral and anti-bacterial vaccines are more effective because the amount of antibodies produced by the animal increases significantly. In the case of breeding animals the amount of antibodies deposited in the egg yolk, milk or colostrum also increases, which is of benefit to the offspring.

Preparation of Contamination-Resistant Feedstuffs

Applying formaldehyde to animal feed to kill Salmonella was known before the method of Bland et al., however, previously the goal was merely to provide an immediate killing effect. Formaldehyde solutions were mixed thoroughly with the feed in sufficient quantity to kill the Salmonella, using the same spray equipment ordinarily used to apply mold inhibitors. Such spraying equipment is designed to produce a coarse spray, i.e., droplet sizes in the range 260–400 microns, to decrease energy requirements and increase the application rate. The need to distribute formaldehyde throughout the feed was understood, because more than 99% of the Salmonella should be killed to prevent it from quickly recontaminating the feed. Coarse spraying with large amounts of formaldehyde is adequate for that purpose. Bland et al. discovered that when aqueous formaldehyde is sprayed onto feed in the form of a mist, using an atomizing sprayer, the resulting feedstuff is substantially more resistant to recontamination by pathogenic bacteria than feed treated with the same quantity of formaldehyde using conventional spray nozzles. In each case all of the bacteria are killed immediately, but the misting method produces a strong residual killing effect. It was also observed that much less formaldehyde is necessary to obtain equivalent resistance levels, in terms of the time a sample can resist challenge under aerobic conditions with *E. coli* or Salmonella.

It is possible to characterize a difference in physical properties between contamination-resistant feeds used in the present invention and feeds treated with formaldehyde using conventional spray nozzles. The quantity and distribution pattern of a formaldehyde adduct in the feed can be measured using an acidic hydrolysis assay. A highly uniform distribution of adduct, expressed in terms of the coefficient of variation (CV), is related to the feed's contamination resistance.

The formaldehyde adduct's distribution pattern through the feed is controlled by the size of spray droplets used to apply the formaldehyde, the thoroughness and speed of mixing the feed during the application process, the rate at which the formaldehyde solution is applied, and the residence time of feed in the mixer. A compromise must be reached with regard to some conflicting variables. For instance, it is desirable to move feed through the mixer as quickly as possible for economic reasons, but too short a residence time results in inadequate mixing even if the flow rate of formaldehyde solution is increased. The residence time in a two-ton (1814.4 kgs) horizontal mixer is typically three to five minutes. The formaldehyde solution should be delivered at a rate of 20–40 gal/hr. (75.5–151.4 liters/hr.). The size of spray particles is preferably small, 20–80 microns. However this range limits flow rate and may require several nozzles. Larger spray sizes, up to about 250 microns, can also be effective if other variables are adjusted to compensate, such as increased mixing rate or residence time, increased amounts of formaldehyde solution, or accepting a decreased resistance to contamination of the finished feed. Typically the best compromise will be a spray particle size in the 10–200 micron range. Suitable application rates for 1 kg of solution per metric ton of feed span the range of 15–90 seconds, preferably 45–60 sec.

The coefficient of variation should be 7% or less to achieve significant resistance to pathogenic bacteria, preferably 5% or less. The term "resistant to contamination by pathogenic bacteria" means that a challenge with 1000 colony forming units (CFU) per gram of feed results in the death of substantially all the bacteria within 24 to 72 hours. In particular, the term "resistance to contamination by Salmonella or *E. coli*" means that a challenge with 1000 CFUs of Salmonella or *E. coli* per gram of feed results in 1 CFU or less per 25 grams of feed after 24 hours incubation at 25° C. A value of 5% CV or less allows reduced quantities of formaldehyde to be maximally effective. Also, such uniform formaldehyde distribution results in much less emission of formaldehyde vapor from the freshly treated feed and appears to increase the yield of adduct. Bacterial resistance is a function of the coefficient of variation. At 7% CV, the product will have relatively low resistance, which also varies according to the quantity of formaldehyde applied. At 4 lbs. (1.81 kg) dry wt. of formaldehyde per metric ton of finished feed a 7% CV results in about 30 days resistance as measured by challenge with *E. coli* (1000 CFU/gram of feed). Conversely, at 2.0% CV and only 2 lbs. (0.91 kg) dry wt. of formaldehyde/metric ton, a finished feed will resist contamination by *E. coli* (1000 CFUs/gram of feed) for about 60 days.

The increased bacterial resistance of feedstuffs according to the invention can be seen in the following experiment reported in Bland et al., U.S. Pat. No. 5,505,976. A sterilized poultry starter mash (500 grams/treatment quantity level) was treated with 37 wt. % formaldehyde solution in quantities of 0.66, 1.33 and 2.00 pounds (0.30, 0.60 and 0.90 kg) dry weight of formaldehyde per ton (907.2 kg). One set of samples was treated with a coarse spray (270 microns) at 1.8 gal/hr. (6.81 liters/hr.) and another was treated with fine mist (43 microns) at 25.5 gal/hr. (96.5 liters/hr.). Each sample of 500 grams was challenged with 20 ml of a liquid inoculum of *Escherishia coli* (>$10^6$ CFU/ml) one week after treatment. The feed treated with a coarse spray quickly became contaminated with *E. coli* whereas all quantity levels of the 29. feed treated with a mist were free of detectable levels of *E. coli* within 48 hours of the inoculation and for another 60 days, after which the test was discontinued. An experiment using 20 ml of inoculum containing Salmonella ($10^3$ CFU/ml) for recontamination gave similar results.

Most types of bacteria can be recovered from feed for assay purposes by placing a representative feed sample in an isotonic solution, such as buffered phosphate or saline, and plating this solution on a selective microbiological media. The inoculated media is incubated to visualize the bacteria. Some bacteria, such as Salmonella, may require selective pre-enrichment and/or enrichment steps to recover low levels of bacteria and damaged or stressed cells prior to selective media plating.

Suitable major ingredients of animal feed include cereal grains such as corn, grain sorghum, wheat, barley, oats, vegetable protein meals and animal by product meals. Complete animal feed products can also be treated with a mist of aqueous formaldehyde to produce an animal feed of the present invention. A typical complete feed would be a mash or pelletized feed containing corn, soybean meal, minerals, vitamins and other micro ingredients having a total of 7–22% protein, 3–6% fat, 2–5% fiber and an energy value of 1300–3500 kcal/gram.

Many different contamination-resistant animal feedstuffs can be used in the present invention. They are scientifically formulated for the species and age of animal being fed. For example, a laying hen diet would have more calcium in it than would a broiler finisher diet. Production of the feed is usually done in a mixer where all ingredients are added by weight then mixed. The immune response of the relevant animals can be enhanced with formaldehyde-treated turkey grower feed, chick starter feed, sow feed, dairy cow feed, feed for fish, shrimps, eels, etc.

The quantity of formaldehyde applied to the feedstuff is in the range 0.20–4.0 pounds (0.09–0.18 kg) dry wt. of formaldehyde per ton (907.2 kg) of feed, preferably 0.66–1.32 pounds (0.30–0.60 kg). A feed major ingredient should contain from 100 to 1000 grams of formaldehyde adduct per ton (907.2 kg). A complete feed product should contain about 100–660 grams of adduct per ton (907.2 kg). Formaldehyde is commercially available in 37 wt. % aqueous solution. One gram of this solution contains 370 mg or 12.3 mmol of formaldehyde.

The preferred mist or atomized spray consists of droplets in the size range 10–250 microns, preferably 20–200 microns and most effectively 40–80 microns. Spray nozzles capable of delivering these droplet sizes are commercially available. The preferred nozzles are those in which the liquid is supplied to the nozzle under pressure and compressed air is mixed with the liquid to produce a completely atomized spray. The droplet size is a function of air pressure and liquid pressure, so that a single nozzle can provide different sprays if desired. Particle droplet size can be reduced by increasing the air pressure to liquid pressure ratio. Droplet sizes at the different ratios can be determined by laser optics techniques using e.g., model OAP 2D GA2 manufactured by Particle Measuring Systems, Boulder, Colo.

A sufficient number of nozzles should be used to cover the surface of the feed in the mixing vessel. Para-formaldehyde is an insoluble condensation product of formaldehyde that should be removed prior to application of the solution to avoid clogging the spray apparatus. The solution preferably contains a $C_1$–$C_8$ alcohol such as methanol, ethanol, propanol, butanol, pentanol, hexanol, heptanol, octanol or phenol in the range 5–15 wt. % to stabilize the formaldehyde.

The aqueous formaldehyde solution can contain additional ingredients conventionally used to preserve animal feed, such as 5–15 wt. % $C_1$–$C_8$ carboxylic acids or salts thereof including formic acid, acetic acid, propionic acid, butanoic acid, benzoic acid, sorbic acid and lactic acid. Suitable salts include alkali, alkaline earth, calcium, sodium and ammonium. The solution may also contain natural terpenes in a concentration of 0.5 to 2.0 wt. %, which may also require 0.5 to 2.0 wt. % of a surfactant to solubilize the terpene. Terpenes are thought to help the formaldehyde penetrate the bacterial cell wall during the initial sterilization process.

Feedstuffs referred to in this invention preferably have a moisture content from 5 to 20%. Higher water content provides an ideal environment for subsequent bacterial growth making it difficult to prevent recontamination of the feed. The water content is usually between 6–14 wt. % most preferably below 12%. The moisture level of feed can be determined by measuring the moisture weight loss that occurs during heating of feed at 110° C. for 16 hours.

Spray application of the formaldehyde solution to the feedstuffs is done at ambient temperature, which can range widely from winter to summer, but normally is in the range of 5° C. to 40° C. Subjecting the treated feed to increased temperature in the pelletizing process is acceptable and does not destroy the effectiveness of the treatment.

Vaccines of the present invention include those composed of killed or attenuated (modified live virus) viral particles, which are produced by several companies including Fort Dodge Animal Health, Pfizer, Bio-immune, Merial-Select, ASL, Intervet and Shearing-Plough Animal Health Corp. There are numerous other vaccine products available in the United States and elsewhere. The vaccines which are commercially available and commonly used include vaccines against Marek's disease, Newcastle disease-infectious bronchitis, laryngotracheitis, avian encephalomyletis, fowl pox, pseudorabies, influenza, transmissible gastroenteritis, porcine reproductive and respiratory syndrome, foot and mouth disease and parvovirus. This list is not all-inclusive.

Bacterins are killed or attenuated bacteria suspended in an aqueous, or oil emulsion or adjuvant type formulation. This type of vaccination is usually administered by subcutaneous, intramuscular or nasal/oral routes. The companies which produce viral vaccines also typically produce bacterins. The bacterins which are commercially available and commonly used include *Salmonella enteritidis, Salmonella cholerasuis, Streptococcus suis, Escherichia coil, Mycoplasma galliseptum, Mycoplasma hyopneumonia,* Erysipelas, Bordetella, Leptosprias species, *Actinobacillus pleuropneumonia* and Haemophilis species. This list is not all-inclusive.

Poultry vaccines can be administered in a number of ways. Inactivated or killed-virus vaccines must be given by injection to each individual bird, which is relatively expensive. Mass vaccination with live-virus vaccines is more economical. Poultry can be immunized by administering live-virus vaccines in the drinking water or aerosol. With the drinking-water and aerosol methods, it is possible to vaccinate large numbers of birds without handling each one. The methods, however, are not without pitfalls. Live viruses used in water vaccination produce mild infections and should be given only to healthy birds. Sick or heavily parasitized poultry may not develop protective immunity. If these conditions are present, it is advisable to postpone the vaccination until the flock has recovered. The exact vaccination protocol is given by the manufacturer of each product. In general, chicks are treated as follows.

| AGE | DISEASE | ACTIVITY |
|---|---|---|
| Days | | |
| 1 | Marek's Disease (MD) | Marek's disease vaccine. Administered at hatchery; under skin back of neck. |
| 10 | Newcastle | Combination Newcastle-bronchitis (ND-IB) vaccination recommended throughout program. Method of administration optional: spray, DW (drinking water), IO (intraocular), or IN (intranasal) route. |
| 35 | Disease-Infectious Bronchitis (ND-IB) | |
| Weeks | | |
| 6 | Laryngotracheitis (LT) | Birds must be 6 weeks or older to develop immunity against a laryngotracheitis (LT). If used earlier, revaccination (IO route) is indicated. |
| 8 | Avian Encephalomyelitis (AE) | Vaccination is primarily for breeder flocks. May be given up to 4 weeks prior to start of production by the DW route. |
| 10 | Fowl Pox (FP) | Fowl pix (FP) vaccination earlier than 6 to 10 weeks of age will not assure lasting immunity. Use WW (wing web) route. |
| 10 | Fowl Pox (FP) | Fowl pix (FP) vaccination earlier than 6 to 10 weeks of age will not assure lasting immunity. Use WW (wing web) route. |
| 12 | Fowl Cholera (FC) | Fowl cholera (FC) bactarin is a killed preparation and may require two injections. Use SC (subcutaneous) route. |
| Months | | |
| 3 | ND-IB | Combination ND-IB vaccination must be repeated at 3-month intervals in both breeder and layer flocks to maintain protective immunity.* |
| 6 | | |
| 9 | | |
| 12 | | |
| 15 | | |

In general, mature chickens are vaccinated as follows:
First vaccination
ND (B-1) and IB (modified Massachusetts via DW, IO, or IN route only.
4 weeks later (repeat at 3-month intervals)
ND (LaSota), IB (regular Massachusetts or Massachusetts-Connecticut) via DW, IO, or IN route.
In breeder flocks the high antibody level obtained by repeated vaccinations and maintaining the flock on contamination-resistant feed will assure transmission of a uniform parental immunity to the offspring.

EXAMPLE 1

Laying hens (17 weeks old) were received from a pullet growing operation and placed in 7 cubic foot (0.20 cubic meters) wire cages (2 birds/cage). Hens were fed 100 g/day of a layer diet shown below, either untreated or sprayed with 1000 ppm formaldehyde.

TABLE 1

BREEDER DIET COMPOSITION

| INGREDIENT | POUNDS |
|---|---|
| Corn | 1321.71 |
| Soybean meal (48% protein) | 453 |
| Limestone | 142 |
| Dicalcium phosphate | 35.14 |
| Poultry fat | 34 |
| Sodium chloride | 9.65 |
| Choline chloride | 1.4 |
| DL-Methionine | 1.0 |
| Vitamin Pre-mix | 1.0 |
| Trace Mineral Mix | 1.0 |
| TOTAL | 2000 |

Protocol for Spray Treatment

Poultry layer mash (200 lbs) (90.72 kg) was treated with 0 (control) or 1000 ppm of formaldehyde in a laboratory-scale double ribbon mixer equipped with an atomizing spray nozzle. There were 5 replicate pens/treatment. Water was supplied ad libitum. Birds were vaccinated with the *Salmonella enteritidis* bacterin of Example 2 intramuscularly at 19, 21 and 23 weeks of age. At 23 weeks of age, the hens were in the second week of lay and eggs were collected three times a week for ten weeks. A total of 120 eggs were collected per replicate.

Antibody levels in the eggs were determined by extracting the yolk with buffered phosphate solution and defatting the supernatant with chloroform. The antibody was further diluted (1:100) and the titer measured by an enzyme-linked immunoassay (ELISA). The results are shown in Table 2.

TABLE 2

Egg Antibody Titer in Response to Bacterin Vaccination of Laying Hens maintained on a Formaldehyde-Treated Feed

| Treatment | Replicate | Antibody titer (O.D.) | Coefficient of Variation (%) |
|---|---|---|---|
| Control | 1 | 0.917 | 10.7 |
| | 2 | 0.948 | 2.6 |
| | 3 | 0.926 | 9.2 |
| | 4 | 0.914 | 14.7 |
| | 5 | 0.907 | 12.1 |
| average | | 0.922 | 9.8 |
| Formaldehyde- | 1 | 0.956 | 1.6 |

TABLE 2-continued

Egg Antibody Titer in Response to Bacterin Vaccination of
Laying Hens maintained on a Formaldehyde-Treated Feed

| Treatment | Replicate | Antibody titer (O.D.) | Coefficient of Variation (%) |
|---|---|---|---|
| 1000 ppm | 2 | 0.969 | 1.9 |
| | 3 | 0.945 | 1.1 |
| | 4 | 0.951 | 1.5 |
| | 5 | 0.945 | 2.8 |
| average | | 0.953 | 1.7 |

In Table 2 the amount of antibody deposited in the egg yolk increased 3.4%. Also, the degree of variation in antibody concentration among eggs produced on different days was reduced from 9.8% to 1.7%.

EXAMPLE 2

Preparation of *Salmonella enteritidis* Bacterin

1. Preparation of Antigen
1.1 A culture of *Salmonella enteritidis* is streaked on blood agar plates and incubated for 48 hours.
1.2 Cells are harvested by scraping and transferred to 0.1 M phosphate buffered saline containing 0.6% formalin.
1.3 The formalized cell solution is centrifuged at 5000 rpm for 15 minutes.
1.4 The cell culture pellet is dissolved in phosphate buffered saline and transferred to a 50 ml serum bottle for freeze drying.
1.5. The freeze dried material is weighed and a 1 mg/ml suspension is made with phosphate buffered saline. Equal volumes of each suspension are mixed to provide the antigen mixture.
1.6. The antigen mixture is further diluted to 40 $\mu$g/ml with carbonate buffer (1.59 g $Na_2CO_3$ and 2.93 g $NaHCO_3$ in 1 liter deionized water; pH 9.6) for coating of ELISA plates.
2. Immunization of Hens—Primary Immunization
2.1 Dissolve 100 $\mu$g of the antigen in 0.25 ml of phosphate buffer saline solution.
2.2. Add 0.25 ml complete Freund's adjuvant to the solution.
2.3. Mix the solution with the aid of the glass syringe and 22 gauge needle to make an emulsion.
  NOTE: This emulsion has to be complete so that adding a drop of the emulsion to a container of water will not result in dispersion.
2.4. Inject 100 $\mu$l of the emulsion in the pectoral muscle (right and left) and in both leg muscles. A total of 0.4 ml of the emulsion will be injected into each hen using the 3 ml plastic syringe and 23 gauge disposable needle.
2.5 Dispose of used material adequately.
3. Immunization of Hens—Secondary Immunization
3.1. A second immunization is performed at two weeks. The same procedure is followed, but the complete Freund's adjuvant is replaced with incomplete Freund's adjuvant to make the emulsion.
3.2. The antibody levels may be further boosted by a third immunization, if necessary.

EXAMPLE 3—ELISA

1. *Salmonella enteritidis* antigens are produced and bound to ELISA microwells to provide quantitative measurement of antibody titers in vaccinated animals.

2. Equipment
2.1. Costar medium binding EIA/RIA plates
2.2. Eppendorf pippette (100 $\mu$l)
2.3. Costar octapippette (100 $\mu$l)
2.4. Titer tops
2.5. 0.1 M Phosphate buffered saline
2.6. 0.1 M Phosphate buffered saline with 0.6% formalin
2.7. Fish serum (Aqua-Block™)
2.8. Antigen solution (40 $\mu$g/ml)
2.9. Refrigerator (4° C.)
3. Preparation of Antigen Solution
3.1 A culture of *Salmonella enteritidis* is streaked on blood agar plates and incubated for 48 hours.
3.2 Cells are harvested by scraping and transferred to 0.1M phosphate buffered saline containing 0.6% formalin.
3.3 The formalized cell solution is centrifuged at 5000 rpm for 15 minutes.
3.4 The cell culture pellet is dissolved in phosphate buffered saline and transferred to a 50 ml serum bottle for freeze drying.
3.5 The freeze dried material is weighed and a 1 mg/ml suspension is made with phosphate buffered saline. Equal volumes of each suspension are mixed to provide the antigen mixture.
3.6 The antigen mixture is further diluted to 40 $\mu$g/ml with carbonate buffer (1.59 g $Na_2CO_3$ and 2.93 g $NaHCO_3$ in 1 liter deionized water; pH 9.6) for coating of ELISA plates.
4. Procedure
4.1. Add 100 $\mu$l of antigen mixture (40 $\mu$g/ml solution) to each well of the EIA/RIA plate.
4.2. Cover the plate with the self-adhesive titer top.
4.3. Incubate the coated plate for 13–18 hours at 4° C.
4.4. Wash the wells 3 times with the phosphate buffered saline solution.
4.5. Add 300 $\mu$l of the fish serum solution.
4.6. Incubate the plates at room temperature for 4–8 hours and refrigerate overnight.
4.7. Wash the wells 3 times with the phosphate buffered saline solution.
4.8. Blot the plates dry.
4.9. Cover the plate with the self-adhesive titer top and store at 4° C.
5. Reference
Harlow, E. and D. Lane. Antibodies: A Laboratory Manual. Cold Spring Harbor Laboratory, 1988.

EXAMPLE 4

Breeder hens (Avian×Avian breed) were vaccinated with a killed vaccine for infectious bursal disease (IBD), a viral vaccine, at 17 weeks of age, which is prior to the onset of egg production. Egg production started at 19 weeks of age and increased until the hens reached peak production at age 22–23 weeks. Eggs were collected from the hens for hatching and placed in a setter at 37.5° C. for 18 days before being transferred to a hatcher set at 36.1–36.7° C. for 3 days. Chicks hatched after 21 days of incubation and were randomly assigned to 24 pens (6×8 feet) (1.8×2.44 meters) containing 55 birds each. Individual animals were identified with wing bands. Twelve pens were fed a control diet, and twelve pens were fed a diet which had been treated with 1000 ppm of formaldehyde using the procedure of Example 1.

TABLE 3

BREEDER DIET COMPOSITION

| INGREDIENT | POUNDS |
| --- | --- |
| Corn | 1214.94 |
| Corn gluten meal | 85.0 |
| Soybean meal (48% protein) | 314.14 |
| Wheat midds | 103.88 |
| Calcium carbonate | 168.03 |
| Dicalcium phosphate | 25.88 |
| Sodium bicarbonate | 17.69 |
| Sodium chloride | 5.0 |
| DL-Methionine | 4.32 |
| Lysine | 3.91 |
| Choline Chloride | 4.91 |
| Vitamin Pre-mix | 2.00 |
| Trace Mineral Mix | 1.00 |
| Fat | 49.30 |
| TOTAL | 2000 |

On days 0, 7, 14 and 21, one to three cc of blood was collected from five birds/pen and centrifuged at 3000 rpm for 10 minutes. The sera was removed and assayed for antibodies to infectious bursal disease using a commercial immunoassay called "ProFLOK" manufactured by Kirk-Gaard and Perry Laboratories Gaithersburg Maryland. The antibody titers of the chicks was averaged for each time interval and expressed as a percentage of the value on day zero.

TABLE 4

Percent of Day-Zero Antibody Titer in Broiler Chickens Hatched from Hens Maintained on a Formaldehyde-Treated Diet

| | Day 0 | Day 7 | Day 14 | Day 21 |
| --- | --- | --- | --- | --- |
| Control diet | 100 | 32.03 | 12.08 | 1.06 |
| Test diet | 100 | 50.40 | 19.76 | 2.56 |

Table 4 shows that the chicks from hens fed the formaldehyde-treated diet exhibited significantly higher levels of circulating antibodies than the control group, indicating there was more efficient absorption of maternal antibodies from the yolk sac.

EXAMPLE 5

Eggs from broiler breeder hens (Avian×Avian breed) fed the diet of Example 4 were placed in a setter set at 37.5° C. for 18 days before being transferred to a hatcher set at 36.1–36.7° C. for 3 days. On day 18 of incubation, the eggs were vaccinated in ovo with a killed vaccine for infectious bursal disease as in Example 4. The chicks hatched after 21 days of incubation and were randomly assigned to 24 pens (6×8 feet)(1.8×2.44 meters) containing 55 birds each. Individual animals were identified with wing bands. Twelve pens were fed a control diet and twelve pens were fed a diet containing the formaldehyde-treated feed of example 4. On days 0, 28, 35 and 42, three cc of blood was collected from five birds/pen and centrifuged at 3000 rpm for 10 minutes. The sera was removed and assayed for antibodies to infectious bursal disease using the commercial immunoassay, ProFLOK. The antibody titers of the treatment and control groups were averaged for each time interval and expressed as the percentage of their respective day-zero values.

TABLE 5

Percentage of Day-Zero Antibody Titers in Broiler Chicks Raised on a Formaldehyde-Treated Diet

| | Day 0 | Day 28 | Day 35 | Day 42 |
| --- | --- | --- | --- | --- |
| Control | 100 | 1.21 | 41.84 | 116.26 |
| Formaldehyde | 100 | 13.38 | 54.47 | 147.85 |

Table 5 shows that the chicks raised on the formaldehyde-treated feed exhibited higher levels of circulating antibodies than the control group. This result suggests that there was more efficient production of antibodies by the chicks in response to the vaccine. Example 5 is similar to Example 4 in that animals consuming the formaldehyde-treated feed had a more efficient immune response to the vaccine than the control animals.

EXAMPLE 6

A three ton (2721.6 kgs) batch of broiler grower pellets as a complete feed is made as follows. The batch is made in a feed mill using a three ton (2721.6 kgs) horizontal computer controlled mixer. The mixer design is such that the outside hull of the mixer is stationary and the mixing is done by rotating paddles inside the mixer. The ingredients for the batch are individually weighed into the weigh hopper which is directly above the mixer. The batch ingredients weighed into the weigh hopper are shown in Table 6:

TABLE 6

BROILER GROWER DIET

| Ingredient | Pounds |
| --- | --- |
| CORN | 2232 |
| MILO | 1560 |
| SOYBEAN MEAL | 1470 |
| FEATHER MEAL | 120 |
| POULTRY MEAL | 150 |
| FAT | 291 |
| VITAMINS | 6 |
| CHOLINE CHLORIDE 70 | 3 |
| TRACE MINERALS | 6 |
| COPPER SULFATE | 3 |
| DEFLUORINATED PHOSPHATE | 84 |
| LIMESTONE | 31.8 |
| SALT | 13.2 |
| LYSINE | 3 |
| DL METHIONINE | 12 |
| COCCIDIOSTAT | 6 |
| ANTIBIOTIC | 3 |

Once the ingredients are weighed and the mixer is clear of the previous batch, the contents of the weigh hopper are dropped directly into the mixer. This transfer takes only a few seconds. The paddles begin to turn, mixing the ingredients. The mixer hull is equipped with three air atomized nozzles giving droplet sizes in the range of 40 to 80 microns. A formaldehyde solution containing 33% formaldehyde, 10% methanol, 9% propionic acid, 0.5% terpene, 0.5% surfactant and 47% water is sprayed while mixing the ingredients over a period of 40 seconds. The feed is mixed for an additional 4 minutes. After mixing, the feed is dropped from the mixer into a holding tank below, again in a few seconds. The feed is then moved by a screw conveyor to an overhead bin. From this surge bin it is transferred by gravity to a steam conditioning chamber to add moisture to the feed. From there the feed goes to a pelletizer which compresses the mash feed into small firm pellets under pressure and 175° F. (79.5° C.) temperature. After the pelletizer the feed passes through a cooler to lower the temperature of the pellets to near ambient temperature and then on to storage for shipment. A 1000 g sample was challenged with 20 ml of Salmonella (1000 colonies/ml) 28 days after treatment with formaldehyde. Two days later the sample had no detectable Salmonella. The coefficient of variation of the adduct was 2.0% and 390 g/ton (390 g/907 kgs) of hydrolyzable formaldehyde was recovered.

EXAMPLE 7

Measurement of Formaldehyde Adduct in Feed Samples

1. Scope

This test method is suitable for formaldehyde concentrations in the range of 0.2 to 4.0 mg/l in distilled samples which corresponds to eight 160 mg of formaldehyde/kg of feed. For samples with concentrations greater than 160 mg/kg the distillate should be diluted with reagent grade water prior to analysis.

2. Summary of the Method

A feed sample mixed with reagent grade water and phosphoric acid is distilled to release the formaldehyde bound to the feed. An aliquot of the distilled sample is combined with an equal volume of an acetylacetone reagent in a test tube. The tube is capped, shaken and reacted at 60° C. for 10 minutes. After cooling, the absorbance of the solution is read at 412 nm. The concentration is calculated from a curve of standard formaldehyde solutions. The chemical reaction is based on the Hantzsch reaction. Formaldehyde reacts with acetylacetone in the presence of ammonium ion to form the yellow compound 3,5-diacetyl-1,4-dihydrolutidine.

3. Reagents and Materials

Reagent water deionized or distilled water that conforms to Type I or Type II (should be free of formaldehyde, residual chlorine, phenolic compounds and substances that interfere with this test). Acetylacetone Reagent-Weigh 154 g of ammonium acetate into a 400 ml beaker. Dissolve the crystals in a small volume of water. Transfer to a 1 liter volumetric flask. Add 2.0 ml of acetylacetone and 3.0 ml of glacial acetic acid to the flask. Add water to mix thoroughly, and dilute to 1 liter. Store the solution in an amber glass container at 4° C. This reagent will last for three months if properly stored.

Formaldehyde Stock Solution (1000 mg/l). Dilute 2.7 ml of 37% formaldehyde solution to 1 liter with water. This solution should be stored at room temperature in glass amber bottle, and should be standardized every 6 months using the following procedure: Calibrate pH meter with the standard 7.0 and 10.0 pH buffers. Pipet 50.0 ml of the formaldehyde stock solution in a 125 ml Erlenmeyer flask, and add 20.0 ml of sodium sulfite solution. Cap and allow the mixture to stand for 5 minutes. Add a magnetic stir bar, and place solution on magnetic stirrer. Titrate rapidly to a stable end point of pH 9.5 with 0.1N hydrochloric acid. Calculate the concentration of formaldehyde stock solution as follows:

$$\text{HCHO, mg/l} = \frac{(\text{HCl titrant, ml}) \times (\text{HCl, N}) \times (30.03)}{\text{stock formaldehyde, ml}}$$

Perform three replications and calculate the mean concentration. Replicates should agree to within 0.3%.

Sodium Sulfite solution (0.1M) should be freshly prepared. Dissolve 31.5 g of anhydrous sodium sulfite in 150 ml of water and dilute to volume in a 250 ml volumetric flask. Adjust to pH 9.5 with 1N hydrochloric acid.

4. Sampling

Representative feed samples should be protected from light and kept at 4° C. Distilled samples should be collected in amber bottles and kept at 4° C. before analysis with Teflon lined lids.

5. Calibration

Prepare a series of 4 standards in 100 ml volumetric flasks as follows:

| Conc. mg/l | $\mu$l of 1000 mg/l HCHO |
|---|---|
| 0.5 | 50 |
| 1.0 | 100 |
| 2.0 | 200 |
| 4.0 | 400 |

Make up to 100 ml final volume with deionized water. Place 2 ml from each standard into a test tube. Add 2 ml of acetylacetone reagent, cap tightly, shake well, and place the tubes in the water bath at 60° C. for 10+/−1 minute. Remove the tubes from the water bath and cool to room temperature. Amber bottles, test tubes, and lids must be properly washed, rinsed with ethanol, and dried at 130° C. for 2 3 hrs before use to minimize contamination.

Zero the spectrophotometer with water at 412 nm. Measure the absorbance of the standard solutions and samples. The color is stable for several hours. Clean all glassware as soon as possible after using by washing with detergent and hot water, rinsing with hot tap water, followed by distilled water rinse. Drain glassware and place in 130° C. oven for several hours.

6. Distillation Procedure

Weigh 5.0+−0.1 g of sample in a plastic boat. Funnel feed into 1000 ml round flask. Add 200 ml of deionized water to flask. Add approximately 2 ml of 85% phosphoric acid and few glass beads. Connect flask to trap and condenser, turn on cooling water and turn on heating mantle(s). Receive distillate in amber bottles. Stop distilling when exactly 100 ml have been collected. Cap bottles with teflon lined caps and store at 40° C. until analysis by color reaction.

After distilling samples, clean up distillation set up by distilling approximately 100 ml of deionized water in between samples.

Analysis: Measure 2 ml of distilled sample into test tube. Add 2 ml of acetylacetone reagent. Process samples in the same manner as the standards. The formaldehyde concentration of the distilled samples is calculated by reading the milligrams per liter on the standard curve which corresponds to the absorbance of the sample. Calculate the formaldehyde concentration of the feed sample as follows:

$$\text{HCHO, kg/ton} = \frac{\mu\text{g/l of HCHO in distilled sample} \times 0.21/1000}{.005 \text{ kg}}$$

EXAMPLE 8

To determine the variability of hydrolyzable formaldehyde adduct distribution due to different methods of spray application poultry starter mash was purchased from a commercial supplier and split to obtain representative 1000 g subsamples. The subsamples were treated with 1 kg/ton of a 37% formaldehyde solution in a laboratory scale feed mixer equipped with liquid spray nozzles. The liquid spray nozzles delivered a course spray (Experiment 1) or a fine spray (Experiment 2) of the formaldehyde solution. Another sample was prepared in a commercial feed mill (Experiment 3 in the following table). Formaldehyde (33% solution) was applied to 6000 pounds (2721.6 kg) of poultry starter mash in a 3 ton (2721.6 kg) horizontal feed mixer at a rate of 1 kg solution per ton of feed. The formaldehyde was applied by three air atomizing nozzles located on the top of the mixer. The formaldehyde solution was applied in 90 seconds and the feed was mixed an additional 4 minutes. The treated feed was subsampled with a Humboldt sample splitter to obtain ten replicate samples of each type of treated feed. These samples (5 g) were assayed for formaldehyde by the procedure in Example 7. The levels of formaldehyde recovered from the treated feed samples represent the adduct and allow for calculation of a coefficient of variation. The results are presented in the following table.

TABLE 7

Variation in the Concentration of Formaldehyde (kg/ton) Recovered from Feed Due to the Method of Application
FORMALDEHYDE ADDUCT (kg/ton)

| SAMPLE # | EXPERIMENT 1 COARCE SPRAY (1 NOZZLE) | EXPERIMENT 2 FINE SPRAY (1 NOZZLE) | EXPERIMENT 3 FINE SPRAY (3 NOZZLES) |
|---|---|---|---|
| 1 | 0.425 | 0.334 | 0.322 |
| 2 | 0.301 | 0.370 | 0.339 |
| 3 | 0.336 | 0.376 | 0.339 |
| 4 | 0.369 | 0.369 | 0.334 |
| 5 | 0.395 | 0.364 | 0.331 |
| 6 | 0.358 | 0.344 | — |
| 7 | 0.389 | 0.380 | — |
| 8 | 0.423 | 0.380 | — |
| 9 | 0.322 | 0.381 | — |
| 10 | 0.383 | 0.403 | — |
| MEAN | 0.3701 ± | 0.3681 ± | 0.3330 ± |
| STANDARD DEVIATION | 0.0413 | 0.0167 | 0.0070 |
| % COEFFICIENT OF VARIATION | 11.16 | 4.53 | P.11 |

The coefficient of variation was much smaller (2.11% and 4.53%) using the atomizing spray method than in the course spray method (11.16%). In Experiment 1, sample 1 contained 425 grams of formaldehyde adduct per ton while sample 9 contained only 322 grams of adduct per ton. This wide variation indicates that the formaldehyde was not distributed evenly, so there are regions of the feed which received little or no formaldehyde solution. Thus, too little adduct may have formed to prevent recontamination of isolated areas even if the initial contamination was effectively killed.

Obviously, numerous modifications of the invention are possible in light of the above teachings. Within the scope of the appended claims, the invention may be practiced otherwise than specifically described herein.

I claim:

1. A method for increasing the level of antibodies in eggs, colostrum or milk produced by a group of breeding animals in response to a vaccination, comprising: enhancing the uniformity of response within said group to a primary vaccination, by maintaining the group of breeding animals on a diet of contamination-resistant, formaldehyde-treated feed having a coefficient of variation of 7% or less, then subjecting said animals to a secondary immunization with the same vaccine.

2. The method of claim 1, wherein said vaccine is selected from the group consisting of a vaccine against Marek's disease, Newcastle disease-infectious bronchitis, laryngotracheitis, avian encephalomyletis, fowl pox, pseudorabies, influenza, transmissible gastroenteritis, porcine reproductive and respiratory syndrome, foot and mouth disease, and parvovirus.

3. The method of claim 1, wherein said vaccine is a bacterin selected from the group consisting of *Salmonella enteritidis, Salmonella cholerasuis, Streptococcus suis, Escherichia coli, Mycoplasma galliseptum, Mycoplasma hyopneumonia,* Erysipelas, Bordetella, Leptosprias species, *Actinobacillus pleuropneumonia* and Haemophilis species.

4. The method of claim 1, wherein said diet consists of formaldehyde-treated feed having a coefficient of variation of 5% or less.

5. The method of claim 1, wherein the animals are selected from the group consisting of chicken, turkey and duck.

6. The method of claim 1, wherein the breeding animals are selected from the group consisting of cow, sheep, pig or horse.

7. A method for improving the immune response of a group of animals to a vaccine, comprising: enhancing the uniformity of response within a group of animals to a primary vaccination by maintaining said group on a diet of contamination-resistant, formaldehyde-treated feed having a coefficient variation of 7% or less, then subjecting said animals to a secondary immunization with the same vaccine.

8. The method of claim 7, wherein said vaccine is selected from the group consisting of a vaccine against Marek's disease, Newcastle disease-infectious bronchitis, laryngotracheitis, avian encephalomyletis, fowl pox, pseudorabies, influenza, transmissible gastroenteritis, porcine reproductive and respiratory syndrome, foot and mouth disease, and parvovirus.

9. The method of claim 7, wherein said vaccine is a bacterin selected from the group consisting of *Salmonella enteritidis, Salmonella cholerasuis, Streptococcus suis, Escherichia coli, Mycoplasma galliseptum, Mycoplasma hyopneumonia,* Erysipelas, Bordetella, Leptosprias species, *Actinobacillus pleuropneumonia* and Haemophilis species.

10. The method of claim 7, wherein said diet consists of formaldehyde-treated feed having a coefficient of variation of 5% or less.

11. The method of claim 7, wherein the animals are selected from the group consisting of chicken, turkey and duck.

12. The method of claim 7, wherein the animals are selected from the group consisting of cow, sheep, pig and horse.

* * * * *